US010330617B2

(12) United States Patent
Hur et al.

(10) Patent No.: US 10,330,617 B2
(45) Date of Patent: Jun. 25, 2019

(54) WEARABLE SENSOR BADGE FOR TOXIC INDUSTRIAL CHEMICALS

(71) Applicant: Design West Technologies, Inc., Tustin, CA (US)

(72) Inventors: Ryan Hur, Irvine, CA (US); Ramesh Palanisamy, Irvine, CA (US); Jeffrey Kim, Irvine, CA (US); Gary Chen, Chino Hills, CA (US); Wei Li, Irvine, CA (US); Dennis Grudt, Long Beach, CA (US)

(73) Assignee: Design West Technologies, Inc., Tustin, CA (US)

( * ) Notice: Subject to any disclaimer, the term of this patent is extended or adjusted under 35 U.S.C. 154(b) by 0 days.

(21) Appl. No.: 15/867,568

(22) Filed: Jan. 10, 2018

(65) Prior Publication Data
US 2018/0195987 A1    Jul. 12, 2018

Related U.S. Application Data

(60) Provisional application No. 62/444,623, filed on Jan. 10, 2017.

(51) Int. Cl.
*G08B 21/00* (2006.01)
*G01N 27/04* (2006.01)
*G08B 21/14* (2006.01)

(52) U.S. Cl.
CPC ............ *G01N 27/04* (2013.01); *G08B 21/14* (2013.01)

(58) Field of Classification Search
None
See application file for complete search history.

(56) References Cited

U.S. PATENT DOCUMENTS

| 4,705,669 | A | 11/1987 | Tsuji et al. | |
|---|---|---|---|---|
| 5,104,553 | A | 4/1992 | Lorenz et al. | |
| 6,245,296 | B1 | 6/2001 | Ligler et al. | |
| 6,837,095 | B2 | 1/2005 | Sunshine et al. | |
| 8,000,903 | B1 | 8/2011 | Li | |
| 9,804,109 | B2 | 10/2017 | Chien et al. | |
| 2006/0250261 | A1* | 11/2006 | Henrie | G08B 5/36 340/632 |
| 2007/0202012 | A1 | 8/2007 | Steichen et al. | |
| 2008/0238700 | A1* | 10/2008 | Locke | G01N 29/036 340/632 |
| 2011/0226619 | A1 | 9/2011 | Eckhardt et al. | |
| 2013/0104733 | A1* | 5/2013 | Bangera | A62B 23/025 95/8 |
| 2014/0333442 | A1* | 11/2014 | Carney | H04M 1/72527 340/573.5 |

(Continued)

OTHER PUBLICATIONS

Kong, Jing, et al., "Nanotube Molecular Wires as Chemical Sensors," *Science*, vol. 287, Issue 5453, Jan. 28, 2000, pp. 622-625, 4 pages.

*Primary Examiner* — Julie Lieu
(74) *Attorney, Agent, or Firm* — Inskeep IP Group, Inc.

(57) ABSTRACT

A wearable sensor badge utilizes a carbon nanotube (CNT) sensor array for selective sensing of chemicals from naturally diffused air or by sampling air using a pump/fan for higher sensitivity. An embedded microcontroller monitors the resistance of the sensing elements and by using an advanced detection algorithm the presence of TICs and/or CWAs are identified.

14 Claims, 15 Drawing Sheets

(56) References Cited

U.S. PATENT DOCUMENTS

2015/0309535 A1* 10/2015 Connor ................... G06F 1/163
  361/679.03
2017/0169692 A1* 6/2017 Parra ...................... G08B 21/14
2017/0365152 A1* 12/2017 Parra .................... G01N 33/004

* cited by examiner

WEARABLE SENSOR BADGE FOR TOXIC INDUSTRIAL CHEMICALS

RELATED APPLICATIONS

This application claims priority to U.S. Provisional Application Ser. No. 62/444,623 filed Jan. 10, 2017 entitled Wearable Sensor Badge for Toxic Industrial Chemicals, which is hereby incorporated herein by reference in its entirety.

BACKGROUND OF THE INVENTION

The present invention relates generally to the field of chemical and/or biological detection. More particularly, the present invention provides a useful and novel system and method for detecting target toxic industrial chemicals, chemical or biological materials.

Chemical detection finds a wide variety of applications, such as detection of toxic industrial chemicals used in industrial and manufacturing applications, law enforcement and anti-terrorist efforts, environmental and agricultural contamination monitoring, medical diagnosis, and detection of chemical warfare agents.

The usefulness of carbon nanotube (CNT) structures in the field of chemical detection has been demonstrated. CNTs are molecular-scale 'wires'. CNTs-based sensors are capable of detecting small concentrations of gas molecules. The conductance of CNTs can be substantially increased or decreased by exposure to certain gas molecules. Reference: Nanotube Molecular Wires as Chemical Sensors; Jing King, et al.; Science Magazine; Vol. 287; Jan. 28, 2000. Therefore, by measuring the change in an electrical property of a CNT sensors, such as resistance, capacitance, voltage or conductance, it is possible to detect the presence of a chemical that drives a change in that electrical property, and to identify the present chemical by comparing the magnitude, rate and direction of change of the electrical property to those changes known to result from exposure of the sensor to a particular chemical or biological agent.

While fixed sensors may utilize CNT structures to provide some amount of chemical detection, it can often be impractical to mount these sensors at locations throughout a manufacturing facility, combat zone, or other location so as to assure each worker/soldier is free from chemical exposure. Hence, what is needed is a sensor that is small and light enough to be easily carried around by a person, and yet is inexpensive enough such that a large number of workers/soldiers can be provided with one. A disposable configuration of the badge allows the user to dispose of it when contaminated with chemicals after an alarm event.

SUMMARY OF THE INVENTION

The present invention is directed to an apparatus and a method of detecting toxic industrial chemicals (TICs) and chemical warfare agents (CWAs) in the form of gas, vapor, and aerosol using a wearable sensor badge. The wearable sensor badge is capable of detecting the presence of TICs and CWAs, well below the permissible exposure limits (PEL) and immediately dangerous to life or health (IDLH) levels. It can also measure the total exposure of user to selected TICs/CWAs.

The sensor badge utilizes a carbon nanotube (CNT) sensor array for selective sensing of chemicals from naturally diffused air or by sampling air using a pump/fan for higher sensitivity. An embedded microcontroller monitors the resistance of the sensing elements and by using an advanced detection algorithm the presence of TICs and/or CWAs are identified.

The wearable sensor badge warns a user of the presence of TICs and/or CWAs above the PEL and alerts the user if they are exposed to TICs/CWAs longer than the recommended time-weighted average (TWA) exposure limits or when the IDLH is reached. The alarm indicators include visual flashing red light, an intermittent buzzer and vibrator for tactical situations.

The device is powered by a battery (primary or secondary) thereby enabling its operation as an independent device. It can also be powered or recharged using a USB port so as to serve as a subsystem to other sensor systems. A Wi-Fi module of the sensor badge is capable of sending the alarm signal to a smart device or to a remote location.

The principle of detection is based on selective adsorption of target chemicals on to the sensing elements of a sensor array and measuring the electrical resistance changes of the sensing elements. Each sensing element is chemically modified to selectively adsorb target chemicals in order for a selective sensing. Collectively, the sensing elements of sensor array produce a characteristic signal pattern for each TIC or CWA there by eliminating cross sensitivity. The principle of distinguishing TICs from common interferences involves the analysis of adsorption kinetics of TICs on the sensing elements using an advanced algorithm.

The sensor array prepared according to previous section is placed into the sensor housing in which the air is sampled from either naturally diffused air flow towards the sensor or using a mini fan/blower. The temperature and humidity of the outgoing air is monitored using a micro temperature and humidity sensor. The sensor array, mini fan and the micro temperature/humidity sensor are connected to a microcontroller embedded circuit assembly. The microcontroller drives the fan and collects the resistance data from the sensor array and temperature/humidity sensor. The sensor unit is a wearable, inexpensive, hands-free solution for first responders, military, and industrial personnel. The sensor unit or badge is versatile in that it can be worn on current personal protective equipment (PPE) such as gas masks, helmet, and NBC garments and provides visual and audible alarms. The low-power carbon nanotube sensor produces a highly sensitive response to CWA or TIC contaminated air. The analog electrical response of nanotube sensor array is transferred to digital data using an A/D converter. The collected data is then processed using microprocessor according to the detection algorithm stored in the internal memory. If any TIC is detected then the digital alarm signal from the microprocessor is converted to analog signal using a D/A converter and sent to LED/Buzzer circuit to warn/alert the user.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
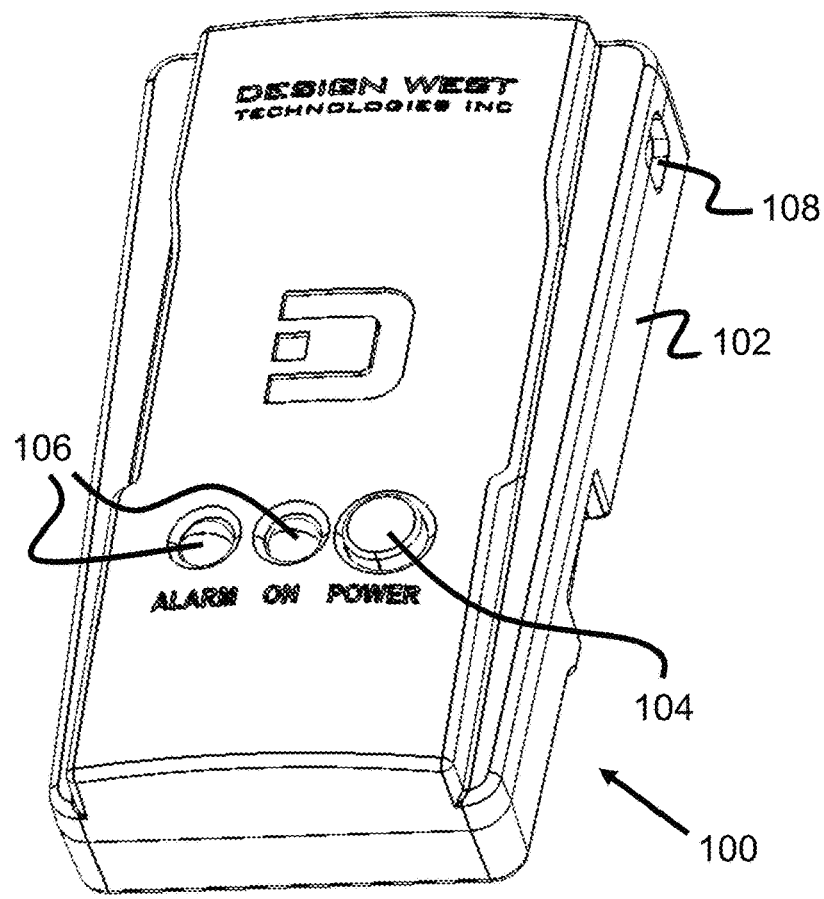
FIGS. 1, 2, 3, 4, 5, 6, and 7 illustrates various views of one embodiment of a wearable sensor unit for detecting toxic industrial chemicals.
Figure 2:
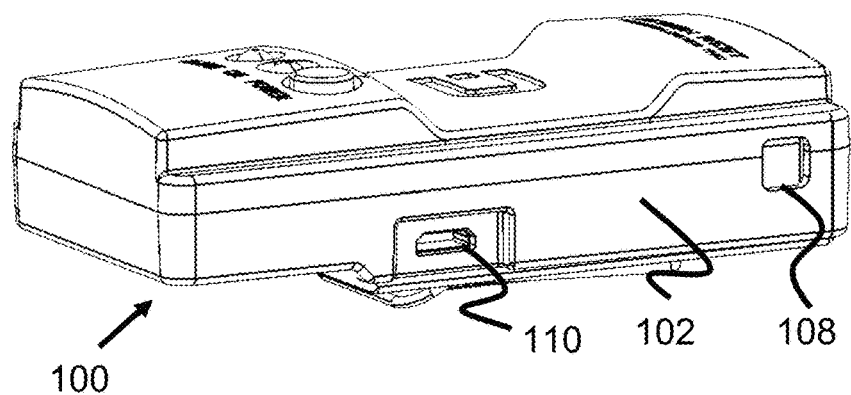
Figure 3:
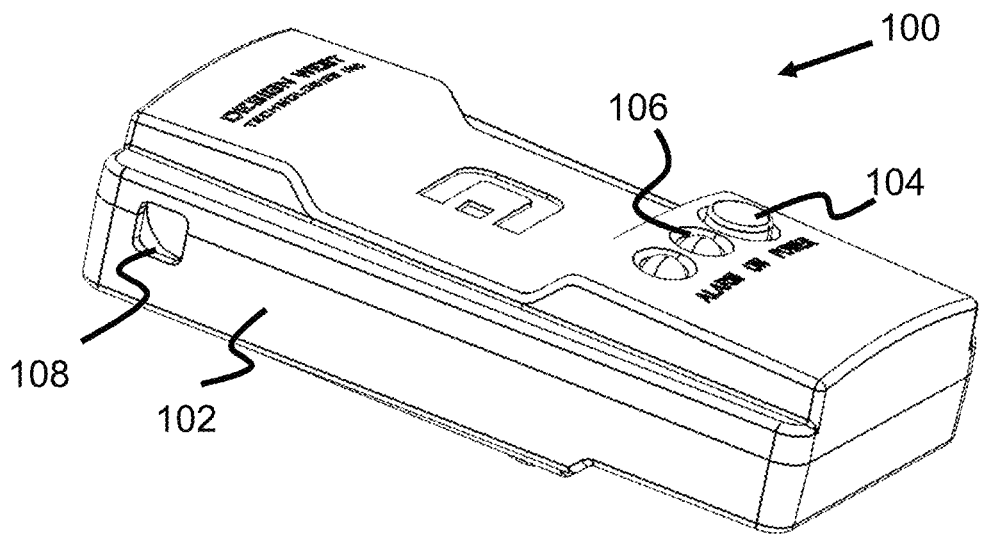

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 4:
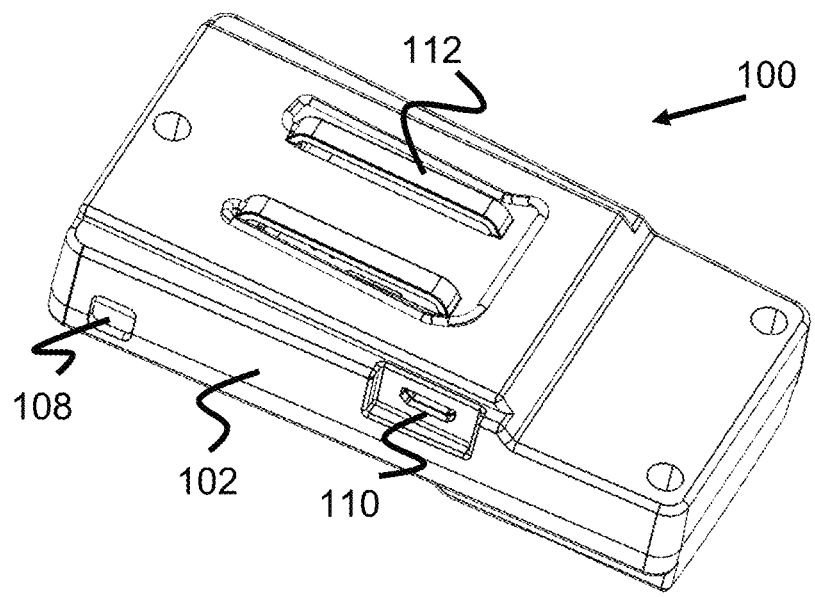

FIGS. 1-7 illustrate various views of a first embodiment of a wearable sensor unit 100 for detecting toxic industrial chemicals (TICs) and chemical warfare agents (CWAs) in the form of gas, vapor and aerosol, as well as monitoring permissible exposure limits (PEL) and immediately dangerous to life or health (IDLH) chemical levels. In one example, the sensor unit 100 has dimensions of about 3.6 inches×2 inches×1 inch, with a weight of about 55 g, which provides a reasonable size and weight for attaching to a user's clothing (e.g., a belt or arm band) via clothing clips 112 (FIG. 4).

The sensor unit 100 includes an outer housing 102 that contains the sensor components and can be formed of several different housing fixtures that removably connect together (e.g., a top housing portion and a bottom housing portion). The top face of the sensor unit 100 includes a power button 104 that turns the sensor unit 100 on/off, and two indicator lights 106 that indicate when the sensor unit 100 is powered on and when there is an alarm condition that the user should be aware of.

In one embodiment, the sensor unit 100 includes a rechargeable battery 122 that can be recharged via an outer power/data outlet 110 (e.g., a USB outlet). Alternately, the battery 122 can simply be replaceable by opening the housing 102, when necessary.

Figure 5:
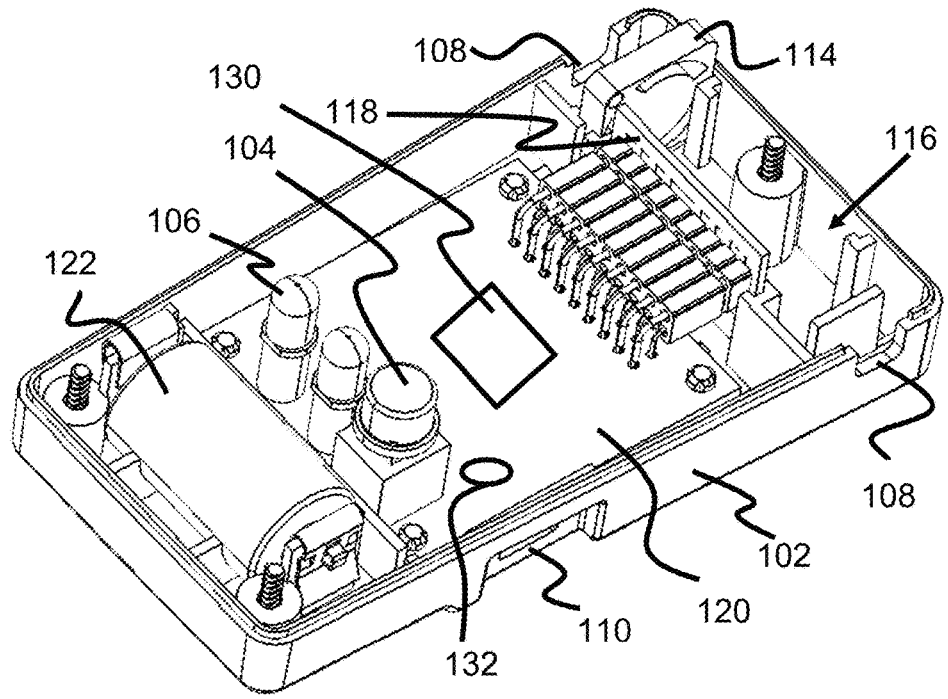
Figure 6:
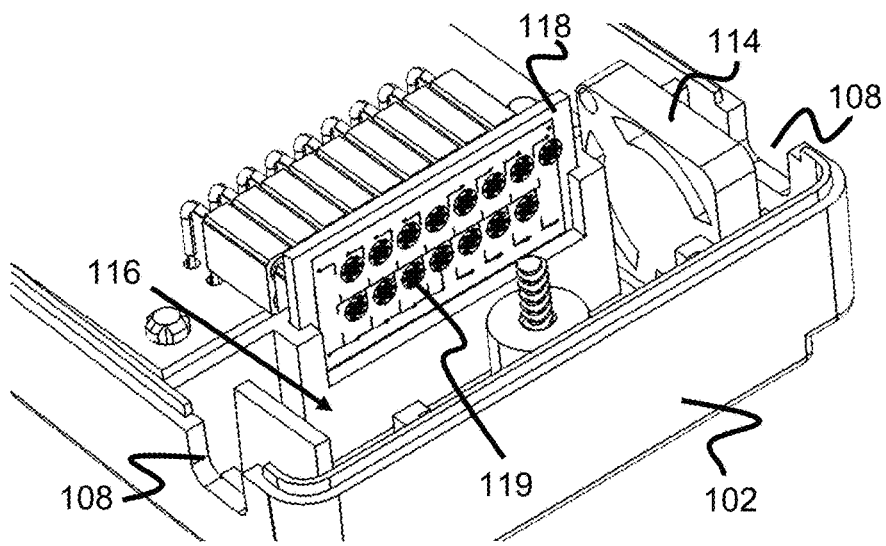
Figure 7:
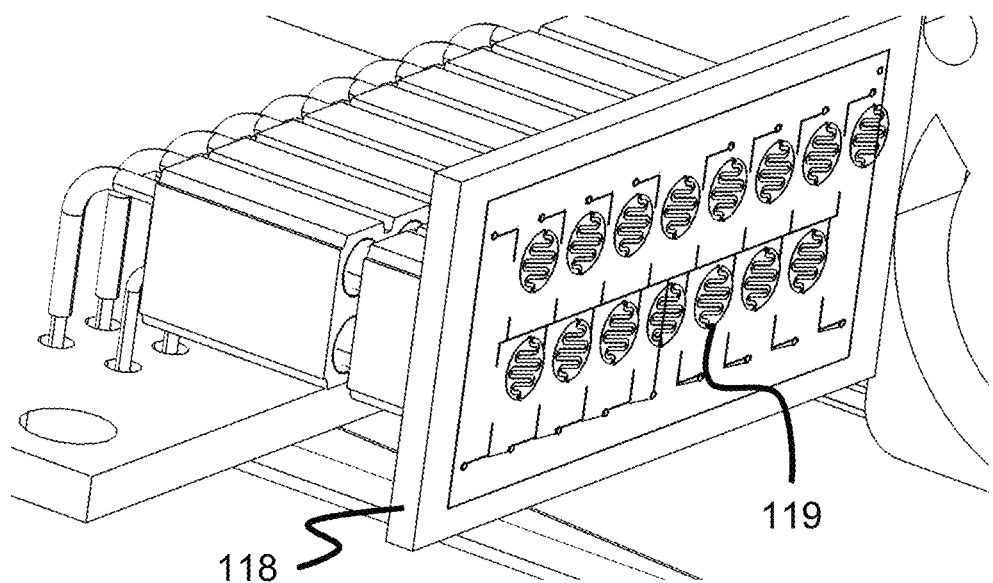
Figure 8:
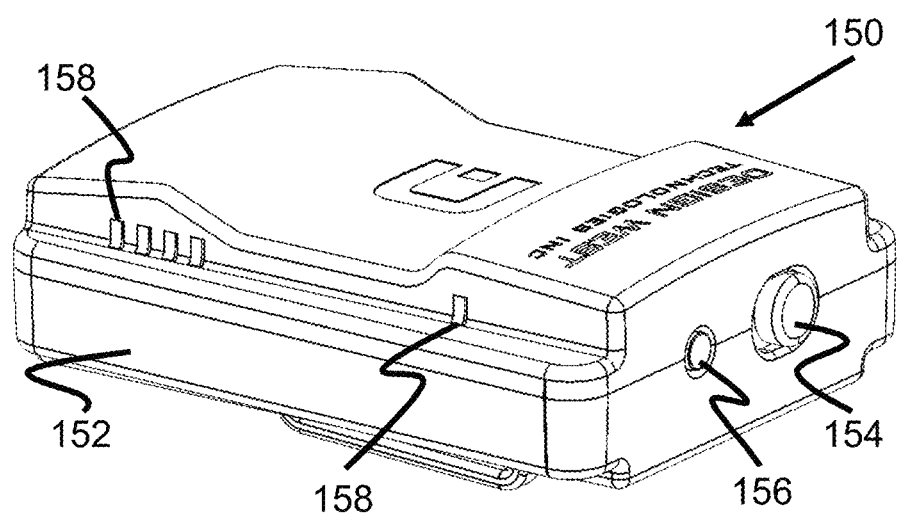
FIGS. 8, 9, 10, 11, 12A, and 12B illustrates various views of another embodiment of a wearable sensor unit for detecting toxic industrial chemicals.
Figure 9:
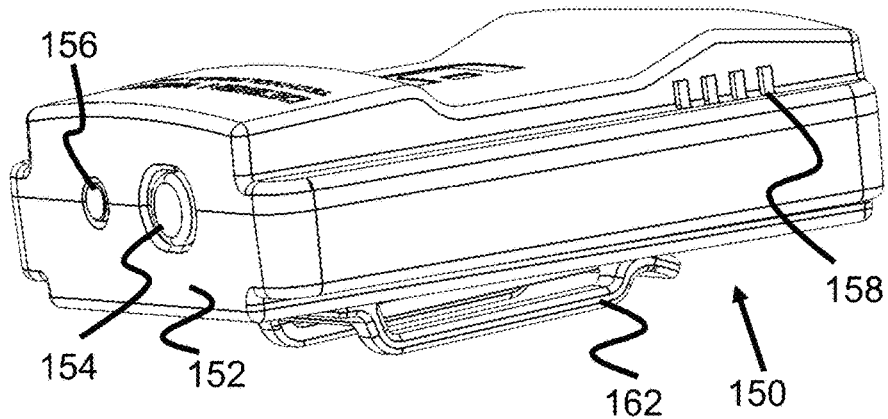
Figure 10:
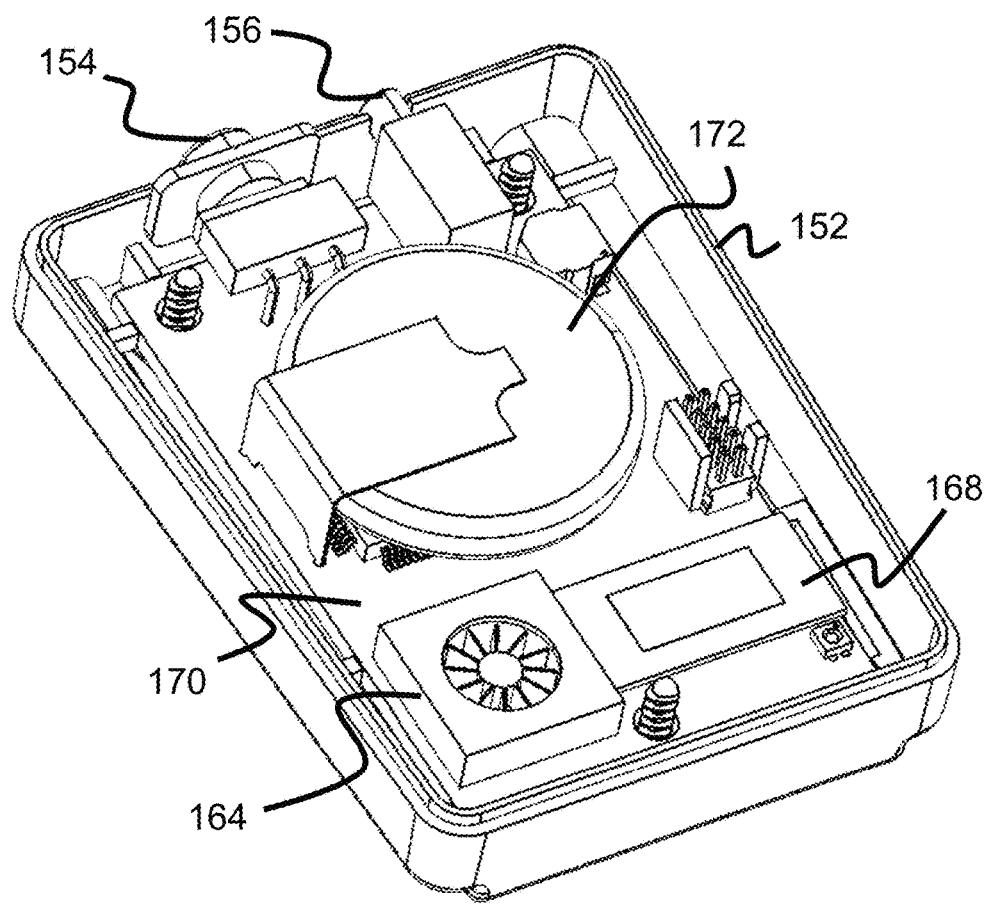
Figure 11:
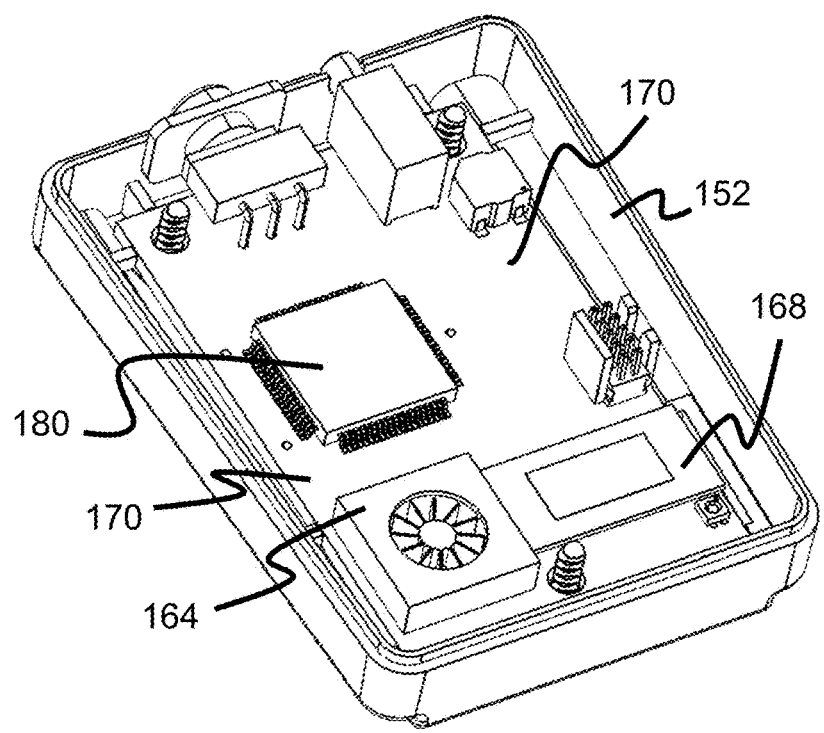
Figure 12A:
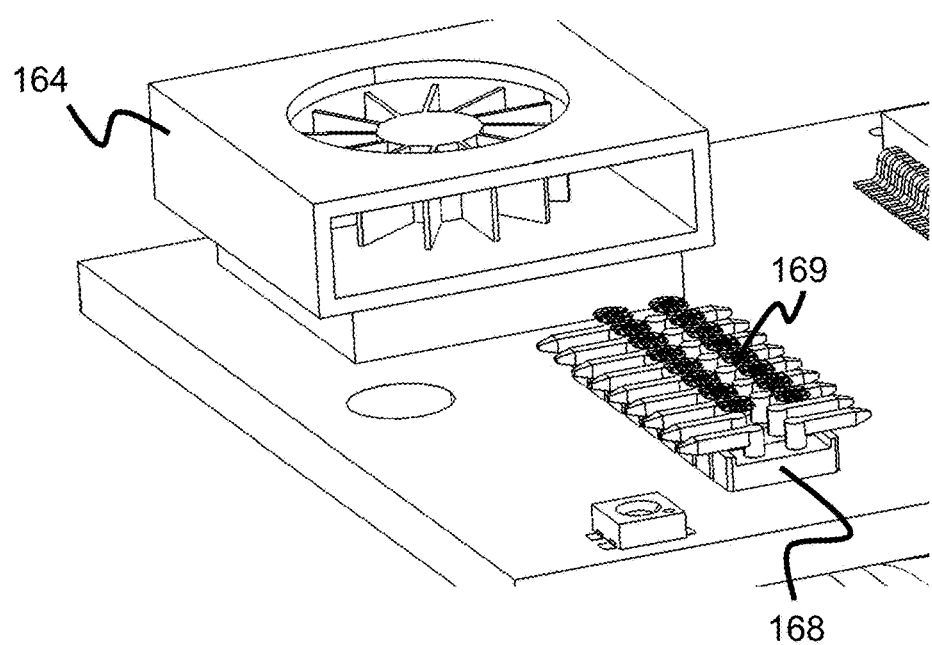
Figure 12B:
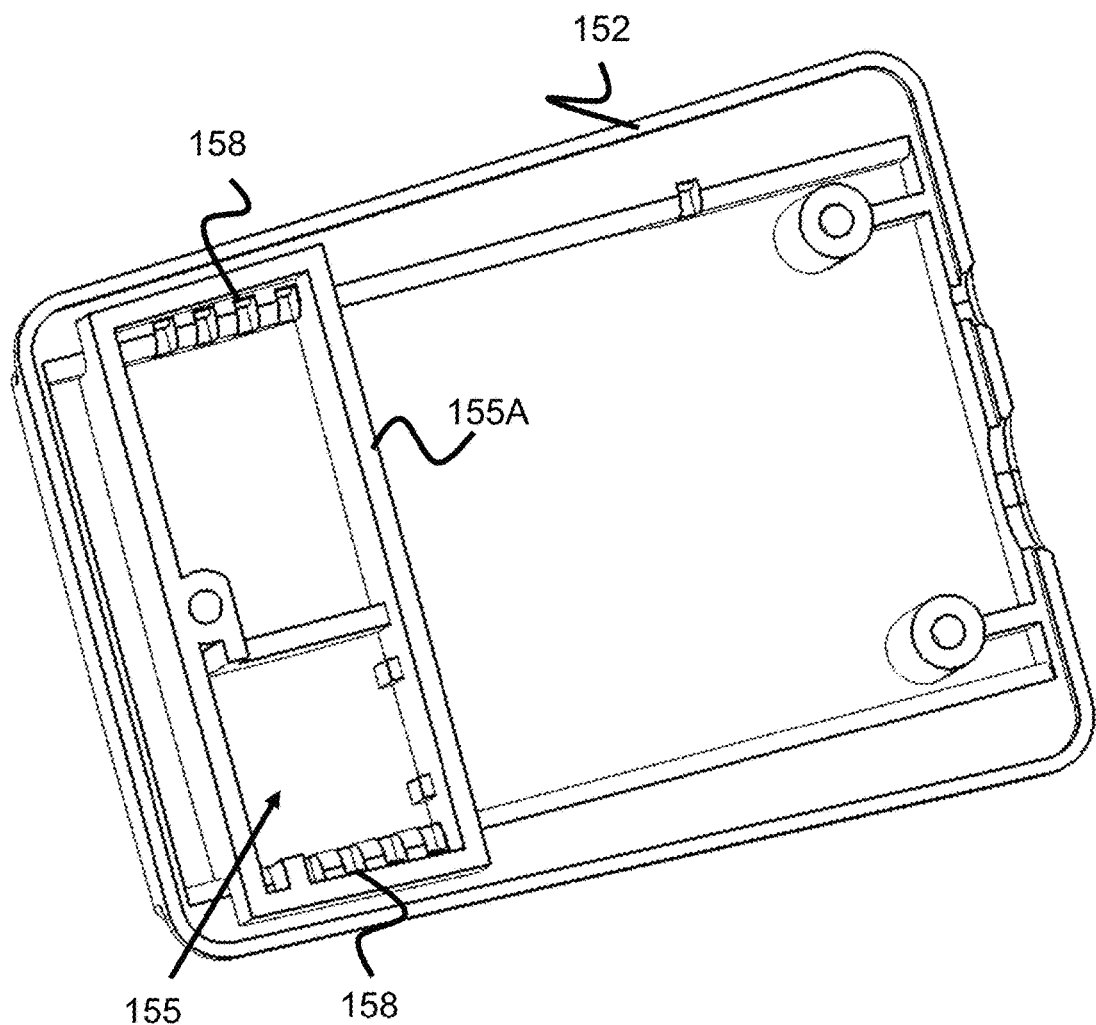

As best seen in FIGS. 5-7, the sensor unit 100 introduces outside air through a flow channel 116 containing a carbon nanotube sensor array 118. A pin header (connector) connects the sensor array 118 to the printed circuit board 120, thereby allowing the sensor array 118 to be removed and replaced. Once closed, the top and bottom portions of the housing forms the flow channel across the width of the unit 100, isolating the sensor array from other electronic components and thereby protecting them from chemical exposure. The flow channel 116 is open on either side of the housing at apertures 108 which allows a sampling pump 114, preferably a low powered fan (e.g., 12 mm×12 mm×3.4 mm), to create an air current through the flow channel 116. The sampling pump 114 can be positioned near and facing one of the apertures 108 to help blow air by the perpendicularly-facing sensor array 118. Preferably, a particle screen can be positioned across each aperture 108 to help prevent intake of large particles that could, over time, clog the unit 100. In an alternate embodiment, the sampling pump 114 is removable (or not included), allowing air to naturally diffuse to the sensor array 118 thereby chemical detection is achieved.

The sensor array 118 is preferably composed of a plurality of different sensors 119 positioned along the array 118 to face the flow channel 116. In one embodiment, the sensor array 118 is fixed in place in a slot (best seen in FIG. 6) and is removable from its connections to the printed circuit board 120, allowing a user to periodically replace the array 118 as needed, Note, further details of the sensor array 118 are discussed in greater detail later in this specification.

The printed circuit board 120 further includes one or more reference resistors. These reference resistors can be used for reference or comparison purposes relative to each of the sensors 119 of the sensor array 118 to determine an accurate sensor reading.

The printed circuit board 120 preferably includes a microprocessor or microcontroller 130 to measure the resistance of the sensor array 118, execute detection algorithms, and control the alarm functions. In one example, the microcontroller 130 includes an integrated 16-bit analog-to-digital converter to measure the resistance of the sensor array 118.

When the algorithms executed by the microcontroller 130 detect an alarm condition, the microcontroller 130 can activate the indicator lights 106 and/or a vibration unit 132 and/or an audible alarm (e.g., via a speaker). Optionally, the circuit board 120 may further include a wifi transceiver, or similar wireless communications device, that is connected to an onsite system that can turn on an alarm for an entire facility/location.

In order to help increase the accuracy of the sensor array 118, a temperature and humidity sensor can be included on the printed circuit board. This allows the microprocessor to be normalized for gas concentrations at different temperature/humidity levels and account for those environmental factors to provide a more accurate concentration reading.

Figure 13:
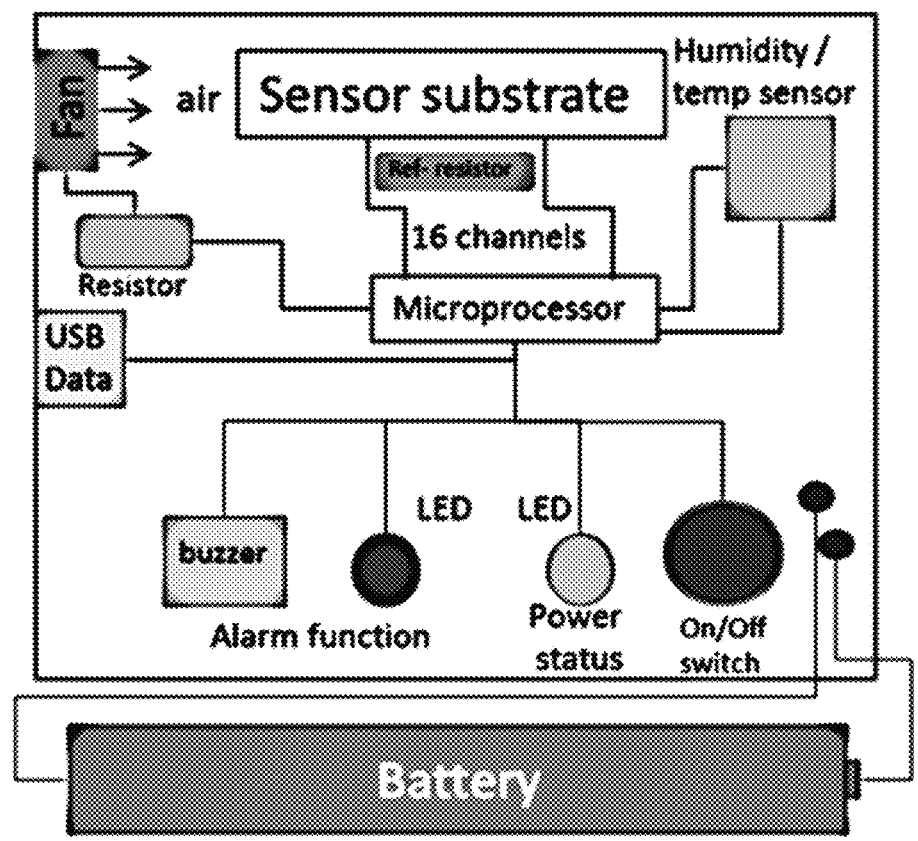
FIG. 13 illustrates a schematic view of the sensor unit of FIG. 1.

The above-described components of the sensor unit 100 can also be seen in their schematic, electrical layout in FIG. 13.

FIGS. 8-12B illustrate another embodiment of a wearable, disposable sensor unit 150 that is generally similar to the previously described sensor unit 100, but having a smaller size (e.g., about 2.25 inches×1.75 inches×0.75 inches; weight 30 g). In this regard, the sensor unit 150 is generally sized similar to a small badge. The small size, inexpensive components, and non-removable power supply allow the unit 150 to be used and then disposed of, which can be particularly helpful if the unit was exposed to toxic chemicals.

The sensor unit 150 includes an outer housing 152, with a power button 154, an indicator light 156 easily visible by the user from the top when mounted on a shirt pocket or belt, and ventilation apertures 158, which are all similar to those of the larger unit 100. A battery 172 (preferably non-removable and optionally rechargeable) is fixed over the microcontroller 180 so as to minimize the overall size of the unit 150.

The lower end of the unit includes a sensor array 168 vertically mounted on the printed circuit board 170 and located next to a sampling pump 164. Unlike the prior pump, this pump 164 a blower-style, mounted horizontally with top air input and a side exhaust port. The side exhaust port is oriented towards the sensor array 168 so as to blow air over its sensors 169 to help allow for accurate readings. The top of the housing 152 has a flow channel 155 formed via the horizontal walls 155A on its inner surface and that connect to the ventilation apertures 158 on each side of the housing.

Once closed, the top and bottom housing forms the enclosed flow channel 155, isolating the sensor array 168 from the other electronic components (e.g., the microcontroller 180) thereby protecting them from chemical exposure.

As previously described with regard to the sensor unit 100, the printed circuit board 170 of the sensor unit 150 can similarly include one or more reference resistors, a vibration unit, an audible alarm, light indicators, a wifi transceiver, and any other previously discussed features.

Figure 22:
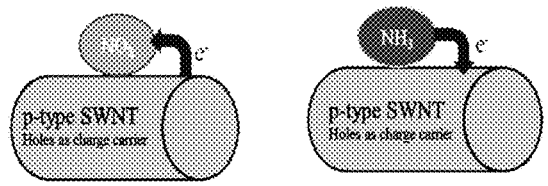
FIGS. 22 and 23 illustrate carbon nanotube sensors used for sensor arrays.

The previously discussed sensor arrays 118, 168 preferably utilize functionalized single walled carbon nanotubes (SWNT) as sensing elements. SWNTs are a seamless cylinder of single layer graphene with a π-electron cloud enriched outer surface due to the curvature, making it highly surface sensitive. Upon adsorption of polar molecule(s) on the nanotube surface, partial charge-transfer is expected to occur and it can be measured as the change of resistance of the nanotube, as shown in FIG. 22. This chemiresistor property of SWNTs can be exploited for selective chemical sensing.

Figure 23:
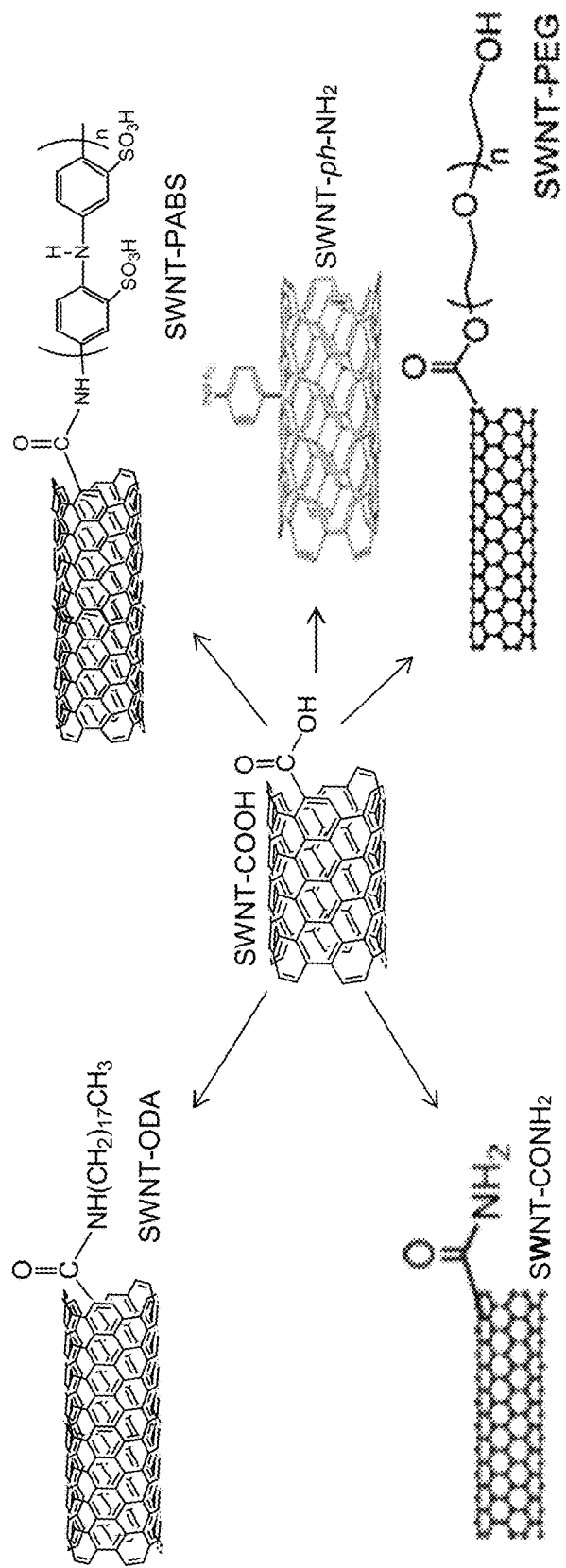

In order to impart selectivity to nanotube, chemical functional groups can be attached by covalent (or) non-covalent modification as shown in FIG. 23 for selective adsorption of analyte of interest. Covalent attachment functional groups both on the edges and sidewall are used. Commercially available SWNTs with covalently attached functional groups such as carboxylic acid (COOH), octadecylamine (ODA), m-polyaminobenzenesulfonic acid (PABS), polyethylene glycol (PEG), amide (—CONH2), nitro phenyl SWNT (SWNT-ph-$NO_2$), and amino phenyl SWNT (SWNT-ph-NH2) have been used as received or modified with metal or metal oxide particles, or with metal salts for improved selectivity.

Generally, these sensors can be created with powder SWNT material that is dispersed in an appropriate solvent (e.g., water or DMF) using an ultra-sonication bath and then centrifuged to obtain SWNT ink. This ink is then deposited on the interdigitated electrodes of the sensor array by a drop cast method. In order to maintain a balance between power consumption and signal to noise ratio, each sensing elements is fabricated within 1-5 kOhm. Each channel is independently wired to measure the electrical resistance during the operation. Additional details of example sensors can be found in U.S. Pat. No. 9,804,109 which is hereby incorporated by reference.

There two example sizes of the sensor array for the previously described embodiments. The first array 118 is larger in size while the 2nd configuration sensor array 168 has a relatively smaller footprint. The weight of the large sensor array 118 is approximately 2.5 g whereas the smaller sensor array 168 is just 1 g. Similarly, the dimension of smaller sensor substrate 168 is much smaller (about 0.75"× 0.35") compared to the large array 118 (about 1.0"×0.5"), nearly a 50% reduction in area usage. Due to the smaller area available for the formulation deposition in array 168, the resistance of each sensor element is higher than its reference resistors. In order to keep the sensor element at the optimum performance temperature (15-30° C.) a micro heater may be incorporated to either sensor array.

Figure 14:
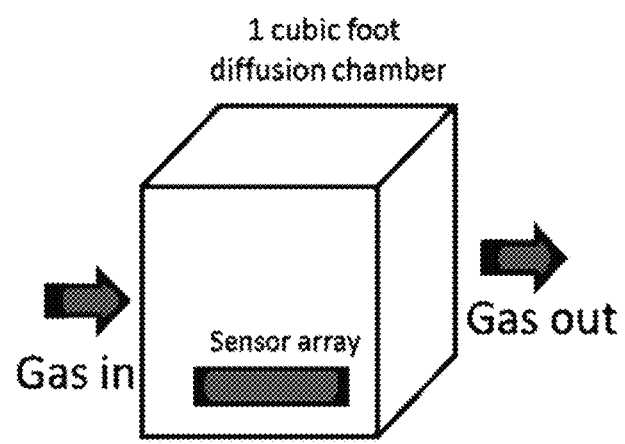
FIG. 14 illustrates a diffusion chamber used for calibration of a sensor unit.

The following describes an example method of calibrating and using the previously described sensor units 100, 150. First, a sensor unit is placed in 1 cubic foot diffusion chamber for collecting the background resistance data (e.g., FIG. 14). The air pump blows air across sensor array while the resistances of individual sensing elements are continuously measured to monitor the background resistance and noise level. Once background resistance is established, it will be noted as the initial resistance R0 (measured at t0) and the signal will be continuously monitored to measure the resistance R1 (measured at t1). The change in the resistance is continuously measured as ΔR=R1−R0 at defined sampling time periods and the ratio of ΔR/R0 is the sensor response which provides the magnitude of the resistance change.

Figure 15:
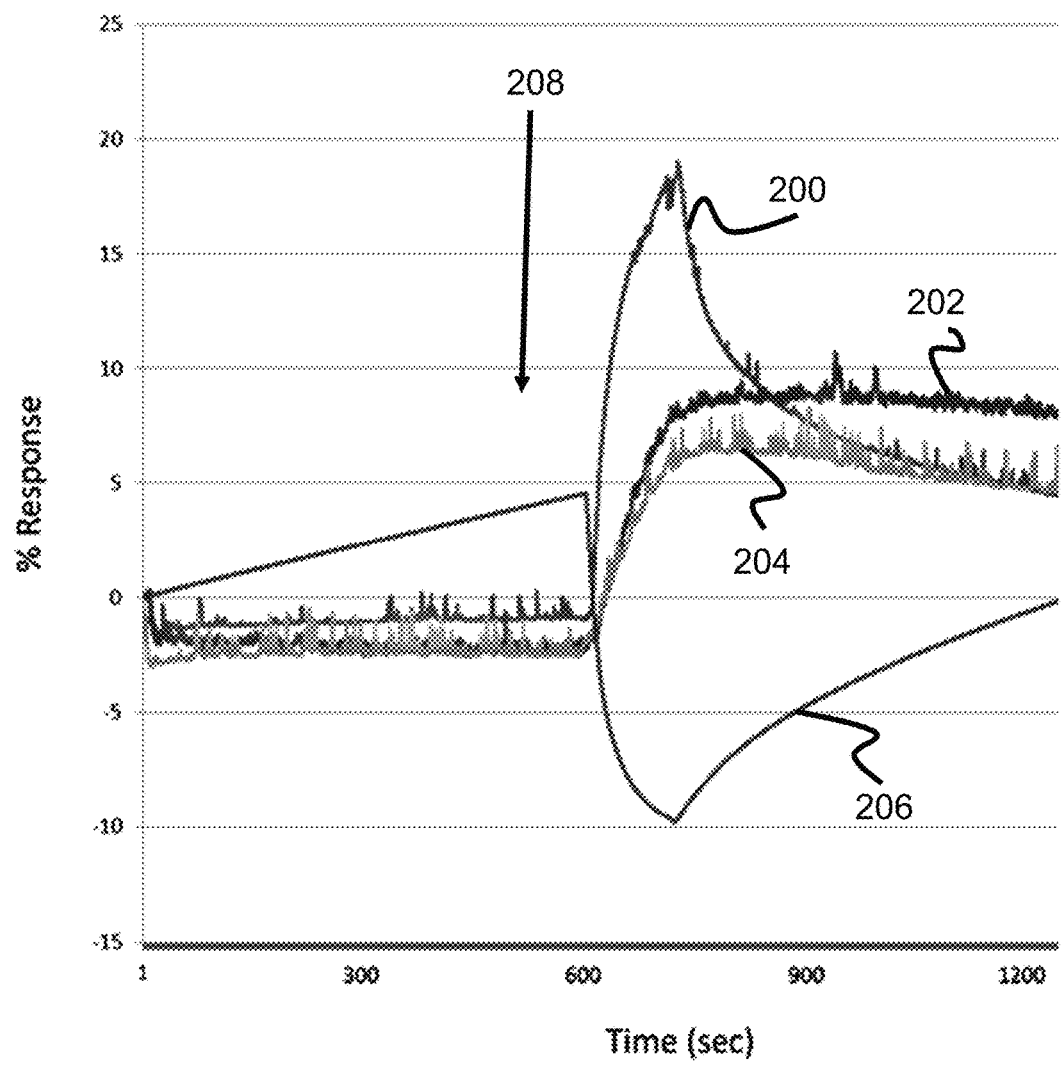
FIGS. 15, 16, 17, 18, 19, and 20 illustrate various graphs relating to calibration of a sensor unit.

Once the TIC gas is introduced to the diffusion chamber the charge transfer between the TIC gas and sensing elements will produce a resistance change, as seen in FIG. 15. Upon TIC exposure the resistance of a sensing element can either increase or decrease depending on the direction of charge transfer between the TIC gas and the sensing element as shown in FIG. 15. In this example ammonia 200, hydrogen sulfide 202, sulfur dioxide 204, and chlorine 206 are used for the testing and analysis, supplied at point 208. Chlorine 206 is the only TIC gas that shows a decreased resistance from the baseline while all other TIC gases show an increase in resistance as shown in FIG. 15.

In order to account for environmental effects, the sensor array is calibrated at low and high humidity at given concentrations of toxic gases. Similarly, the effect of temperature is also recorded for each gas at given concentrations of toxic gases. The sensor array response can then be normalized determine the maximum and minimum response for a particular toxic gas. The other gases that can be detected using the sensor array are carbon monoxide, nitrogen dioxide, nitric oxide, hydrogen cyanide, phosphine and methyl bromide. In addition, vapor and/or aerosol of chemical warfare agents also can be detected. Examples of CWA includes GA (tabun), GB (sarin), HD (sulfur mustard), and VX (nerve agent).

Figure 16:
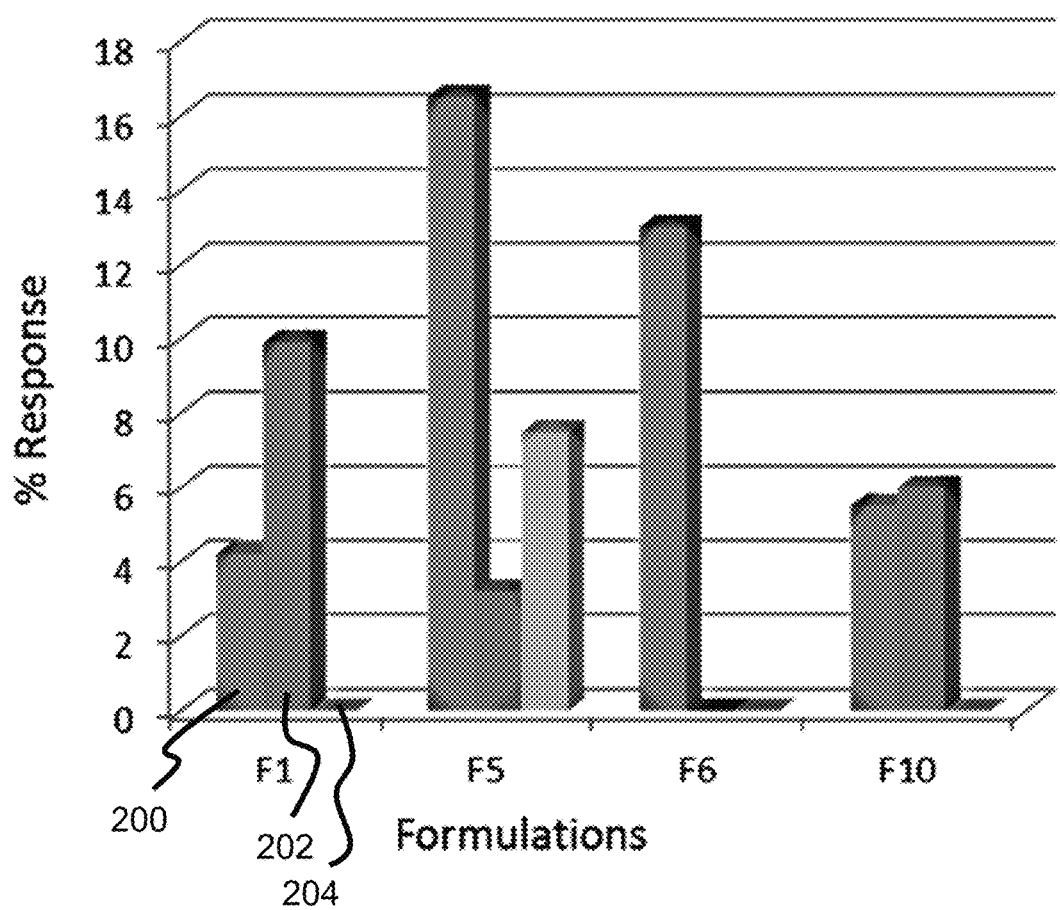

Each toxic gas has a specific normalized maximum and minimum response to each of the formulation used. This provides a matrix of high and low resistance values for a particular toxic gas across the sensor array. In order to identify and distinguish toxic gases (NH3, H2S, and SO2) four sensor formulations have been selected in this example (F1, F5, F6 and F10) which show characteristics response to each of the TIC gas. FIG. 16 shows unique response patterns of the sensor array to three different gases (ammonia 200 first, hydrogen sulfide 202 second, and sulfur dioxide 204 third, for each sensor) and it should be noted that none of them resemble each other. Ammonia shows a response on all of the four formulations, particularly formulation F6 is selective only to ammonia making the identification of ammonia easier among the three TIC gases. While hydrogen sulfide is a known interference to ammonia, it shows responses with three of the four formulations (i.e. F1, F5 and F10). However, both ammonia and hydrogen sulfide show response with F1, F5 and F10 formulations and the selectivity of F6 towards ammonia is the key to differentiate hydrogen sulfide from ammonia. On the exposure of sulfur dioxide to the sensor array, only one formulation (i.e. F5) shows response which helps in the easier identification of sulfur dioxide. When analyzing an unknown gas, the response pattern is compared to the normalized maximum and minimum response of each gas and if it matches to a particular gas then the identity of the gas is found from the pattern recognition algorithm.

Figure 17:
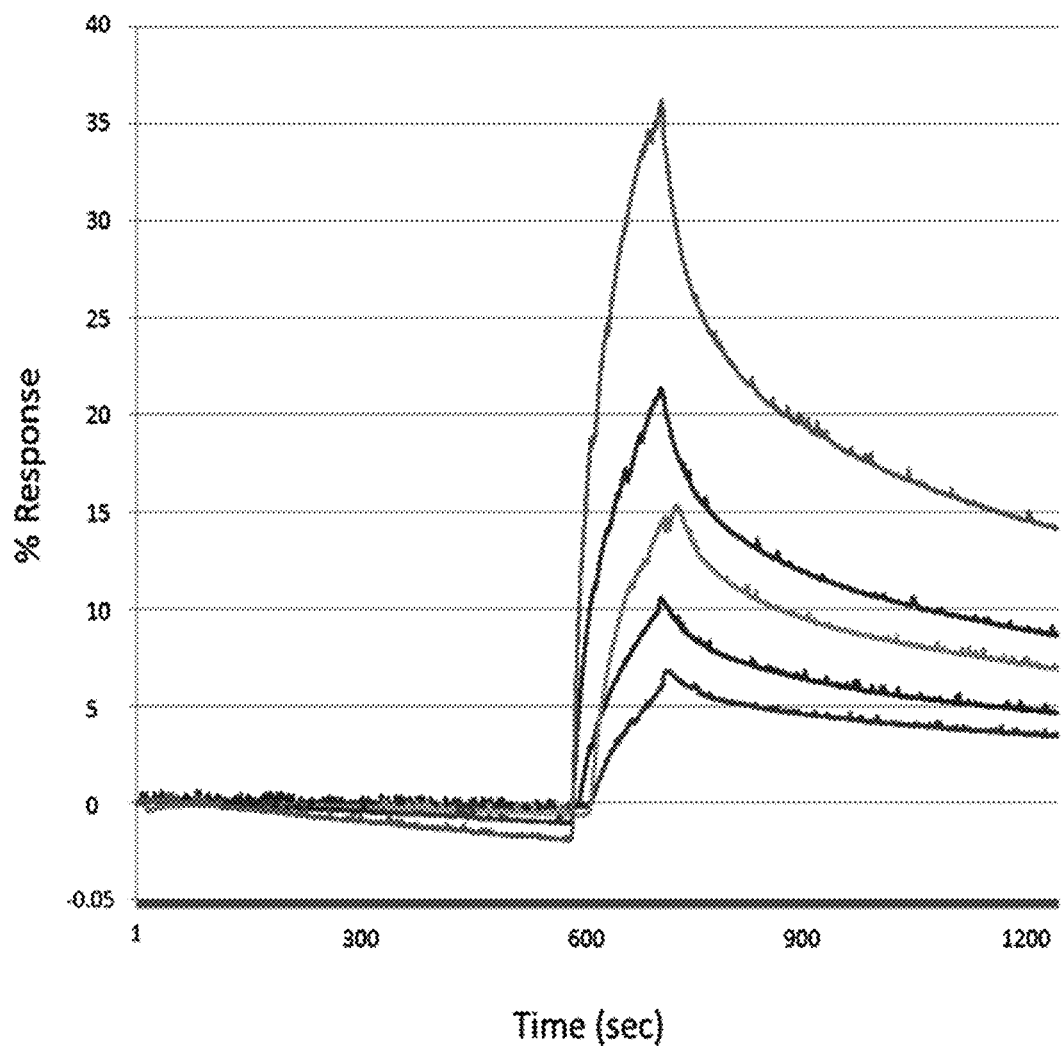

After detecting the presence of a TIC gas based on the resistance change from the sensor array, its concentration is measured to determine if the TIC gas is present above or below the PEL. For this purpose, a calibration plot is previously generated for reference using known concentrations of the TIC gas using the same sensor array. For example, the calibration plot of NH3 generated from the NH3 selective sensor formulation F6 is shown on FIG. 17

Figure 18:
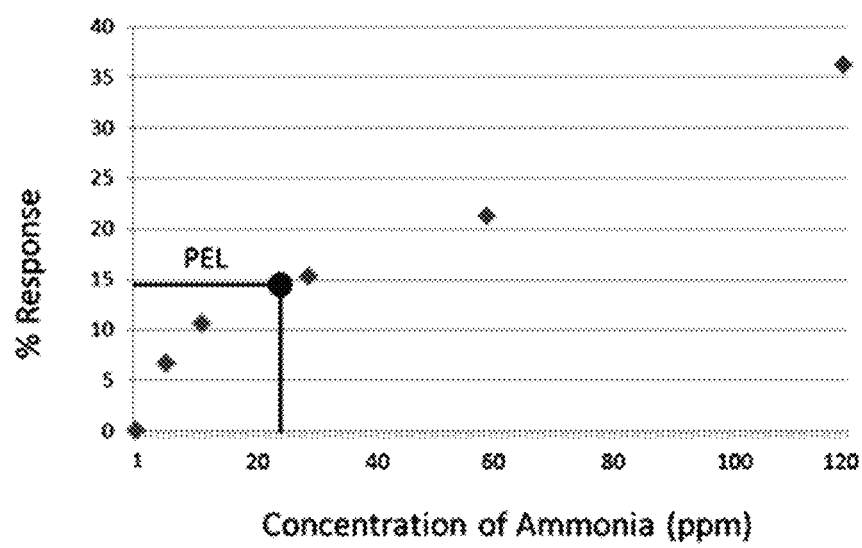

(note, plot lines from top to bottom are: 6 ppm, 12 ppm, 30 ppm, 60 ppm, and 120 ppm). It can be noted that the sensor response ($\Delta R/R0$) is non-linear with the concentration of the NH3. Using the calibration plot, the concentration of NH3 (or other gas) can be tracked, as seen in FIG. 18, and if the response of NH3 exceeds the PEL for that gas, then a warning alarm (level-1) will be generated to notify the user of the presence of TIC and at level-1 the alarm can optionally be muted manually (e.g., vibration, indicator lights, audible alarm, etc.). At a level-1 alarm, the exposure time will be continuously monitored as long as the TIC gas concentration is above the PEL and if the user has exceeded the TWA limit an alert alarm (level-2) will be generated so that the user will have move to a safer place. The alarm will continue as long as TIC gases are detected above the PEL. If the user has exceeded the TWA limit the alarm cannot be muted manually and the alarm can be reset only if the TIC gas level is below PEL. Any time during the use of this badge if the TIC gas concentration exceeds the IDLH level, a level-2 alarm will be generated which alert the user to move to a safer place immediately or to use an appropriate protection gear. For each gas, a calibration plot will be recorded using known concentration of gases and the sensor response will be correlated with the calibration plot for generating the alarm parameter. Using the same principle as ammonia detection all other TIC gases can be detected by first identifying the gas and then verifying the concentration against the calibration plot to generate level-1 or level-2 alarms.

Figure 19:
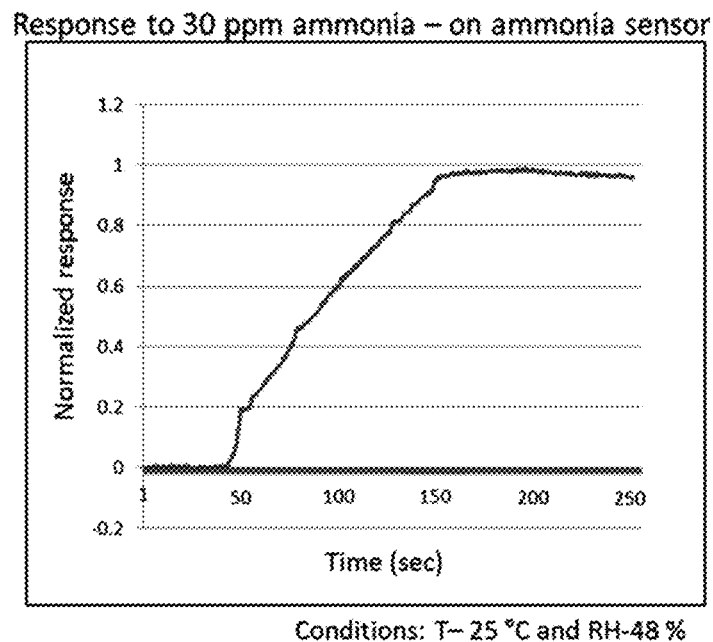
Figure 20:
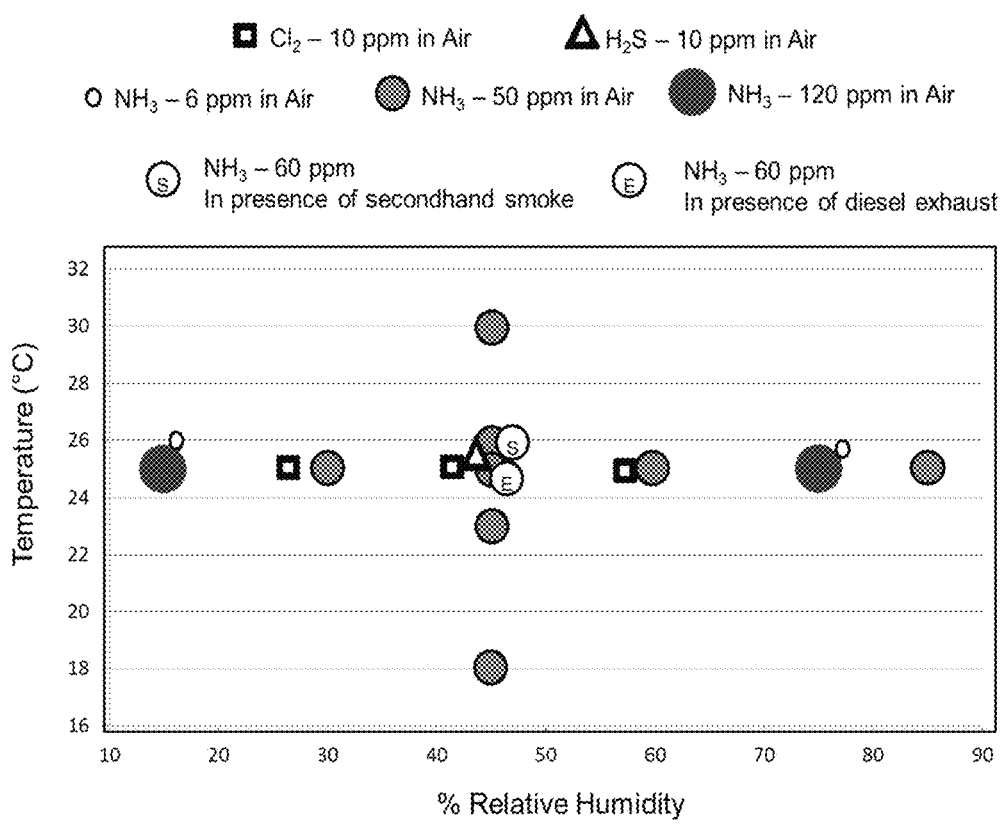

In order to distinguish interfering signals from the actual signal of TIC the response pattern of TIC gases with common interfering chemicals such as diesel smoke and secondhand smoke has been analyzed (FIG. 20). The algorithm used by the microcontroller of the sensor units can distinguish interferences from TICs based on their response kinetics and apply a logic alarm algorithm only if TIC gases are found to be present (i.e., by analyzing the slope of response on FIG. 19 and correlating with the slope established from the calibration experiments). FIG. 20 presents a graphical summary of the results in the temperature-humidity space. Each set of trials is presented by a symbol on a plot. The TIC is color-coded and larger symbols show trials at higher concentration. If an interferent was present, it is shown by a text label "S" for secondhand smoke or "E" for diesel exhaust. Many trials were performed near ambient conditions; the corresponding symbols have been slightly offset for display.

Another important requirement in TIC detection by the sensor units is to monitor the background response continuously to correct for any drift due to environmental factors. For this purpose, a sensing element in the sensor array is included which has no specific functional group for the detection of TICs and therefore serves as a background correction sensor.

Figure 21:
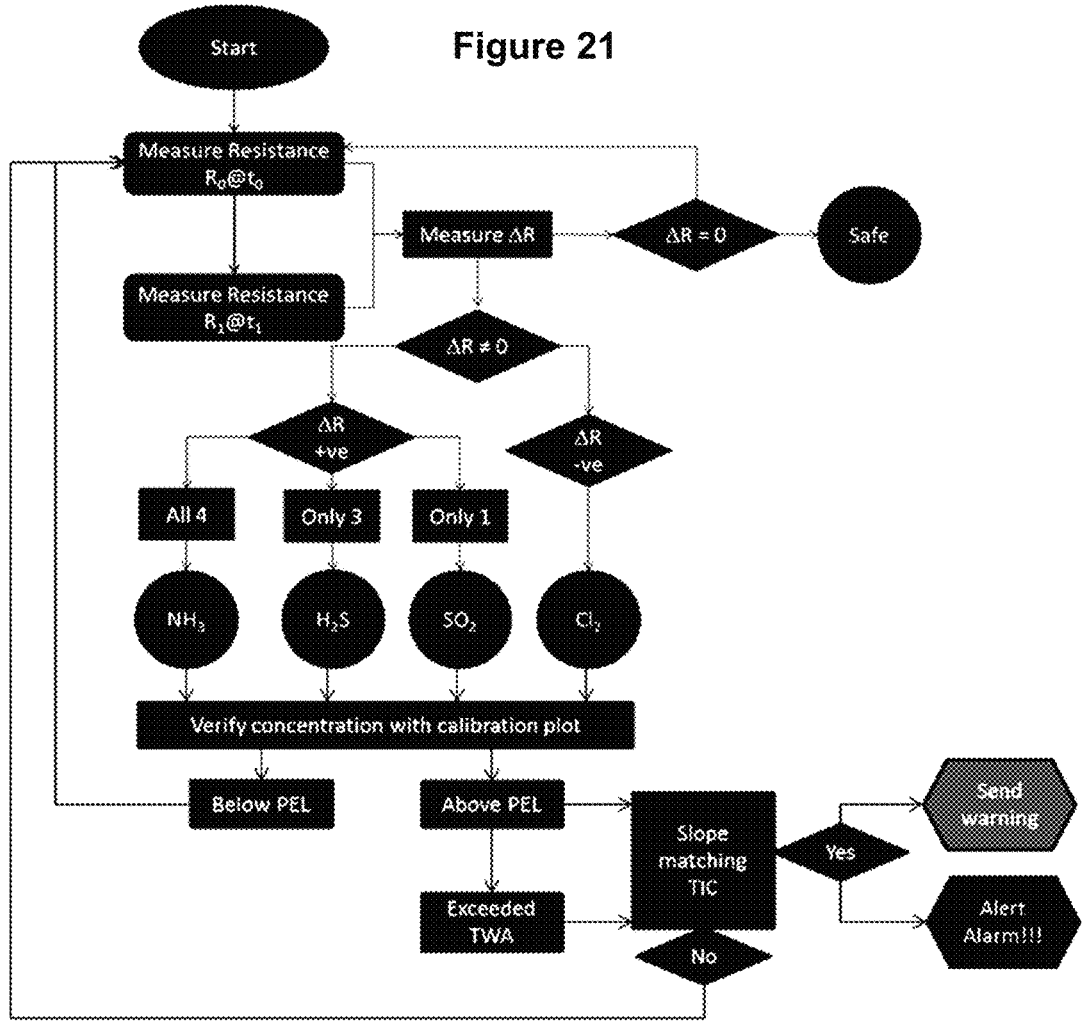
FIG. 21 illustrates an operation flow chart of a sensor unit.

FIG. 21 shows the flow chart of logic parameter to trigger alarm function on the wearable sensor unit. First, the resistance values of the sensor array are measured at a first time and a second, later time. The change in resistance between these times is then determined. If there is no change in resistance, no alarm is triggered and the sensor unit determines that the air quality is safe. If there is a change in resistance values, the changes are analyzed. If the resistance increases on all 4 of the sensors of the array, the unit determines that ammonia is present. If resistance increases on only 3 of the sensors, hydrogen sulfide is determined. If resistance increases on only 2 of the sensors, sulfur dioxide is determined. If resistance decreases on any of the sensors, chlorine is determined. After the presence of a specific gas is determined, the concentration of the gas is determined by referencing a calibration plot stored in memory of the sensor unit. If the concentration is below a PEL, then the sensor unit continues to measure resistance of the sensor array and the prior loop starts again. However, if the concentration is determined to be above a PEL and/or above a TWA by matching the concentration to a PEL or TWA value/slope in memory, then alarm is activated on the sensor unit.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A wearable sensor unit, comprising:
a sensor housing sized and configured for mounting on a person or personal protective equipment;
at least one air aperture opening to an interior of said sensor housing;
a power supply disposed in said sensor housing;
a microcontroller disposed in said sensor housing and powered by said power supply;
a sensor array disposed in said sensor housing and comprising a plurality of carbon nanotube sensors; said sensor array being in communication with said microcontroller; and,
an air pump disposed adjacent to said sensor array and oriented to create a flow of air past said sensor array;
an air flow channel open to an exterior of said sensor housing and containing said air pump and said sensor array; said air flow channel being substantially isolated from said microcontroller;
wherein said microcontroller is configured to monitor said sensor array for toxic chemicals and, when detected, actuate an alert.

2. The wearable sensor unit of claim 1, wherein said sensor array is user removable and replaceable, and is further mounted vertically to a pin header within said sensor housing; and wherein said air pump is vertically mounted perpendicularly to said sensor array and is removable.

3. The wearable sensor unit of claim 1, wherein said sensor array is non-removably mounted horizontally within said sensor housing and wherein said air pump is horizontally mounted adjacent to said sensor array.

4. The wearable sensor unit of claim 1, wherein said microcontroller monitors resistance values of said plurality of carbon nanotube sensors.

5. The wearable sensor unit of claim 1, wherein said sensor array and said microcontroller are configured to detect at least one of ammonia, hydrogen sulfide, sulfur dioxide, chlorine, carbon monoxide, nitrogen dioxide, nitric oxide, hydrogen cyanide, phosphine and methyl bromide, GA (tabun), GB (sarin), HD (sulfur mustard), and VX (nerve agent).

6. The wearable sensor unit of claim 1, wherein said sensor array and said microcontroller are configured to detect at least one of gas, vapor, and aerosol forms of toxic chemicals.

7. The wearable sensor unit of claim 1, wherein said plurality of carbon nanotube sensors are each a single walled carbon nanotube that have a chemical functional group selected from carboxylic acid (—COOH), octadecylamine (ODA), m-polyaminobenzenesulfonic acid (PABS), polyethylene glycol (PEG), amide (—CONH2), nitro phenyl SWNT (SWNT-ph-NO$_2$), and amino phenyl SWNT (SWNT-ph-NH2).

8. The wearable sensor unit of claim 1, wherein said sensor array has dimension of about 0.75"×0.35" or about 1.0"×0.5".

9. The wearable sensor unit of claim 1, further comprising an indicator light exposed on an exterior of said sensor housing.

10. The wearable sensor unit of claim 1, wherein said sensor housing is about 3.6 inches×2 inches×1 inch (55 g), or about 2.25 inches×1.75 inches×0.75 inches (30 g).

11. The wearable sensor unit of claim 1, wherein said wearable sensor unit is disposable when contaminated with chemicals after an alarm event.

12. The wearable sensor unit of claim 1, wherein said at least one air aperture further comprising a first air aperture on a first side of said sensor housing and a second air aperture on a second side of said sensor housing; and wherein said air pump is disposed adjacent to said first air aperture.

13. The wearable sensor unit of claim 1, wherein said microcontroller determines a concentration of gas and then compares sensor values from said sensor array to a predetermined permissible exposure level or a time weighted average.

14. A wearable sensor unit, comprising:
a sensor housing sized and configured for mounting on a person;
at least one air aperture opening to an interior of said sensor housing;
a power supply disposed in said sensor housing;
a microcontroller disposed in said sensor housing and powered by said power supply;
a sensor array disposed in said sensor housing and comprising a plurality of carbon nanotube sensors; said sensor array being in communication with said microcontroller; and, an air flow channel open to an exterior of said sensor housing and containing said sensor array; said air flow channel being substantially isolated from said microcontroller;
wherein said microcontroller is configured to monitor said sensor array, determine a presence of a toxic chemical gas, determine a concentration of said toxic chemical gas, and then compare sensor values from said sensor array to a predetermined permissible exposure level or a time weighted average.

* * * * *